United States Patent
Bastia

(10) Patent No.: US 8,679,007 B2
(45) Date of Patent: Mar. 25, 2014

(54) DEVICE FOR SURGICAL OPERATIONS ON A PROLAPSE

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 322 days.

(21) Appl. No.: 13/120,826

(22) PCT Filed: Oct. 6, 2008

(86) PCT No.: PCT/IT2008/000633
§ 371 (c)(1),
(2), (4) Date: Mar. 24, 2011

(87) PCT Pub. No.: WO2010/041280
PCT Pub. Date: Apr. 15, 2010

(65) Prior Publication Data
US 2011/0201895 A1     Aug. 18, 2011

(51) Int. Cl.
*A61B 1/31*  (2006.01)
*A61B 1/32*  (2006.01)
*A61B 17/02* (2006.01)

(52) U.S. Cl.
USPC ............ 600/215; 600/219; 600/235; 606/197

(58) Field of Classification Search
USPC ................. 600/184, 185, 190, 193, 196, 197, 600/201–203, 205, 210, 212–215, 218, 600/226–228, 235, 245, 121, 123–125, 135, 600/219; 606/197
See application file for complete search history.

(56) References Cited

U.S. PATENT DOCUMENTS

| | | | |
|---|---|---|---|
| 2,922,415 A * | 1/1960 | Campagna | .................... 600/184 |
| 4,966,130 A | 10/1990 | Montaldi | |
| 6,142,931 A | 11/2000 | Kaji | |
| 7,090,079 B2 | 8/2006 | Ehrlund | |
| 2004/0050748 A1 | 3/2004 | Ehrlund | |
| 2006/0167473 A1 | 7/2006 | Scheyer | |
| 2006/0264706 A1 | 11/2006 | Piskun | |
| 2006/0287583 A1* | 12/2006 | Mangiardi | .................... 600/208 |

FOREIGN PATENT DOCUMENTS

| | | | | |
|---|---|---|---|---|
| AD | WO 2007049308 A1 * | 5/2007 | ............... | A61B 1/31 |
| EP | 1683473 A1 | 7/2006 | | |
| RU | 44642 U1 | 3/2005 | | |
| WO | 0238454 A1 | 5/2002 | | |
| WO | 2007019321 A2 | 2/2007 | | |
| WO | 2007094016 A1 | 8/2007 | | |

* cited by examiner

Primary Examiner — Michael T Schaper
(74) Attorney, Agent, or Firm — Pearne & Gordon LLP

(57) ABSTRACT

A device for surgical operations on a prolapse, comprising a hollow stretcher body (2) having a prevalent development direction along a longitudinal axis (A) and being insertable in an orifice, the stretcher body (2) exhibiting a through-window (7), defining an area of intervention and realising a communication between an internal cavity (3) of the stretcher body (2) and a portion of a prolapse, a mobile wall (8) defining the through-window (7) in combination with the stretcher body (2) and being slidably associated to the stretcher body (2) in order to open and/or close the through window (7) between a configuration of minimum extension and a configuration of maximum extension of the through-window (7); characterized in that it comprises means for blocking (10) which act between the mobile wall (8) and the stretcher body (2) in order to maintain the through-window (7) stably in the configuration of minimum extension during insertion of the stretcher body (2).

17 Claims, 3 Drawing Sheets

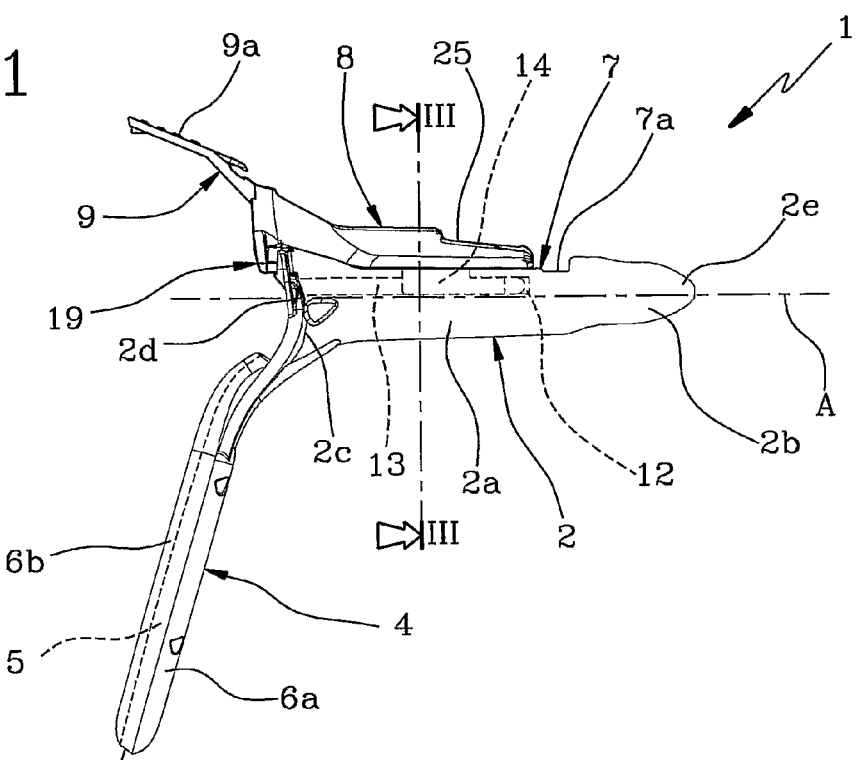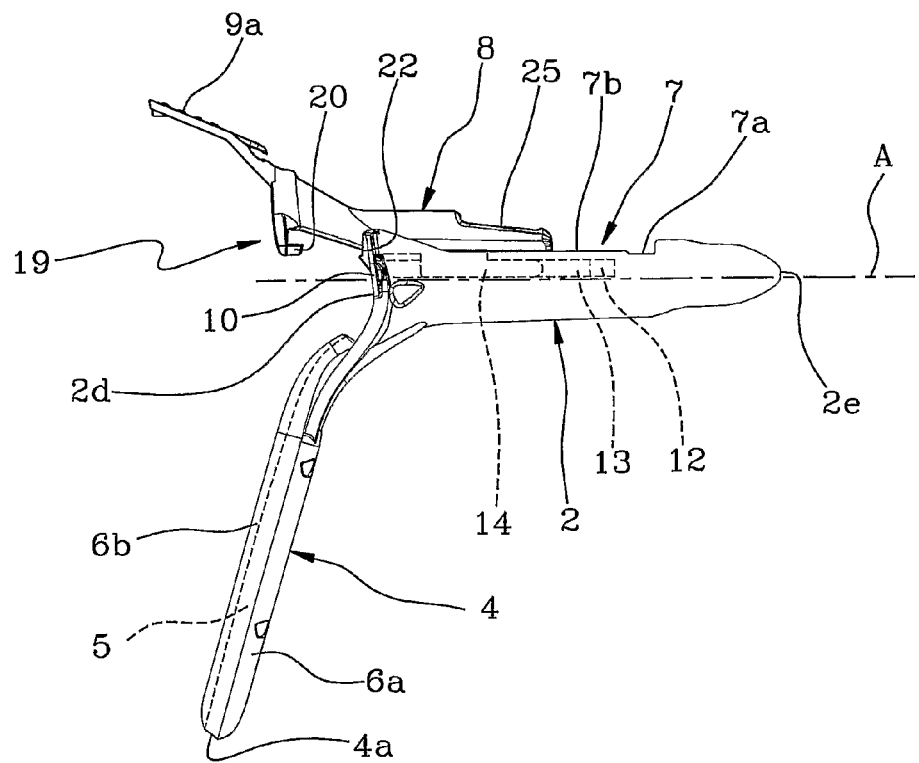

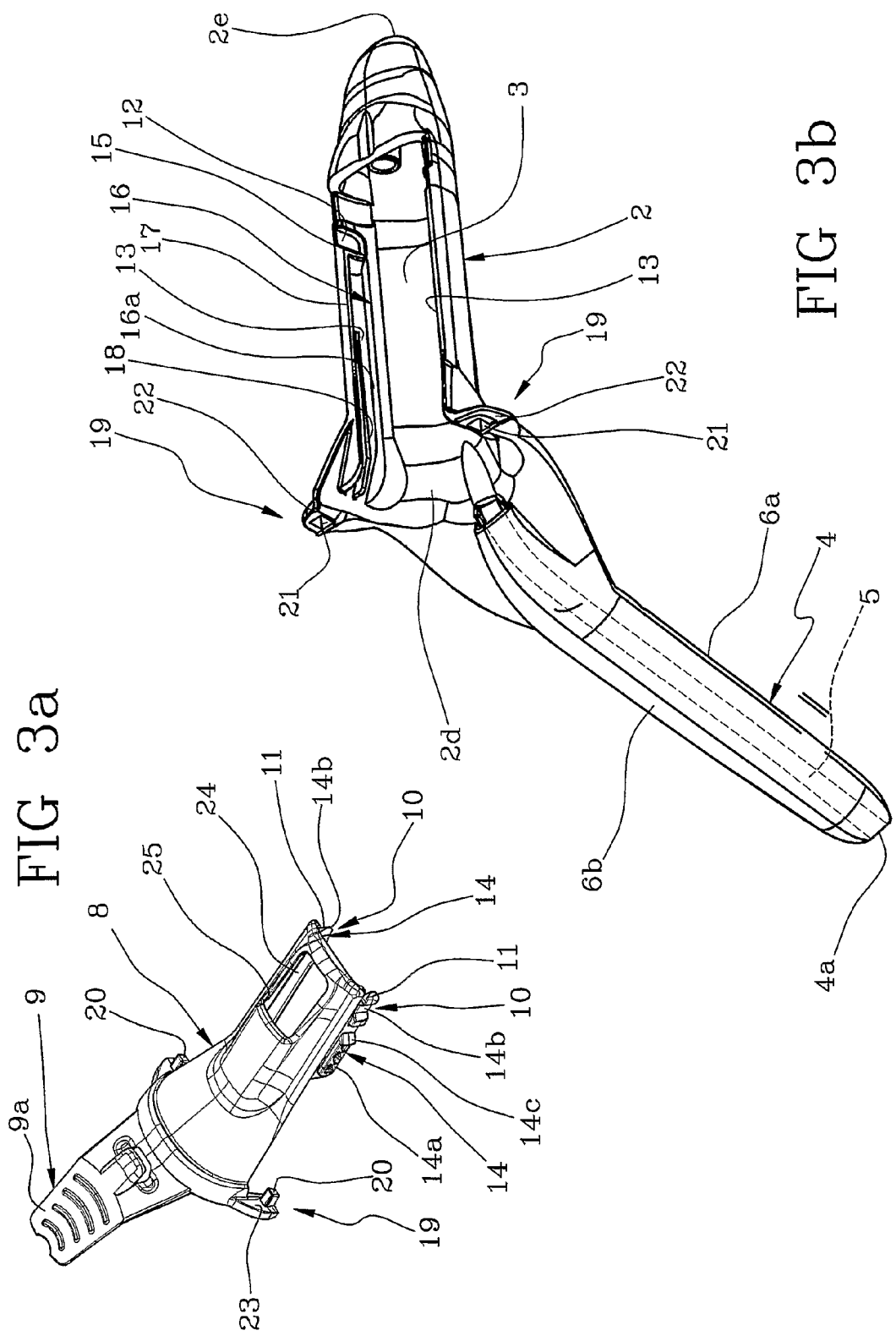

DEVICE FOR SURGICAL OPERATIONS ON A PROLAPSE

TECHNICAL FIELD

The invention relates to a device for surgical interventions on a prolapse.

BACKGROUND ART

The invention concerns the field of surgical operations associated for example to coloproctological pathologies, in particular for treatment and/or reduction of prolapses.

The invention is particularly applicable to operations on mucosa-rectal prolapses, invagination, recto-rectal or recto-anal intususception, or for a total rectal prolapse or anal fissures, peri-anal fistulas, peri-anal abscess, anal tumours or lower rectal tumours.

Without limiting the field of application of the present invention, particular reference will be made to the treatment of haemorrhoid pathologies, diseases which are among the most widespread and known to the public.

As is known, the onset of haemorrhoids begins from pathological alterations of the cavernous bodies of the anal canal, which are formed by vascular lacunae, arterio-venous shunts and saccular venous structures constituting the internal haemorrhoidal plexi. In more detail, the internal haemorrhoidal plexi are hematic lacunae having a calibre of a few millimeters delimited by an endothelium of a venous or capillary type internally of a connective tissue, covered by rectal mucosa. These structures are supported by anchoring fibres to the internal sphincter, known as the Treitz or Parks ligaments.

The cavernous bodies receive a part of the arterial flow from the terminal branches of the upper rectal artery, and this peculiarity has led to the most recent developments in treatment.

The evolution of operating techniques is directed towards intervention of the least possibly invasive type.

The main surgical operation techniques used in the past and still in use, are based on the removal of tissue, i.e. the surgical removal of the portions affected by the pathology, which cannot therefore be included in any category defined as low-invasive.

A first technique comprises identifying and isolating the mucous tissue interested by the prolapse and thereafter the removal of the tissue using forceps.

Once the prolapse has been removed, the technique can include closing the wound by suturing of the lips, or alternatively leaving the resected zone free.

This operating methodology requires a large surgical experience on the part of the surgeon and occasions considerable post-operative discomfort to the patient, connected with the forming of the scar tissue around the wound, and the considerable pain caused thereby.

Another operating technique includes the removal of a portion of rectal mucosa upstream of the zone involved in the prolapse, by means of mechanical suturing.

In more detail, this process includes acting on the rectal wall by means of a ring or circumferential structure, similar to a tobacco pouch in appearance. This is done by suturing several times with thread, up until a portion of circumferentially-developing mucosa located upstream of the prolapse is covered, realising a substantially annular extrusion, which is pronounced towards the inside of the rectal ampulla.

Thereafter the annular extrusion thus realised is resected, by means of a mechanical suturing machine which simultaneously sutures the remaining side-by-side flaps of the mucous wall through the use of metal staples.

In this case too the method described summarily herein above requires very considerable experience on the part of the surgeon and can lead to considerably patient discomfort in the post-operative period, connected to the not infrequent occurrence of complications.

A further surgical intervention technique is based on the surgical occlusion of the terminal part of the upper rectal artery, which interests the prolapse, and a subsequent choking off thereof, with a consequent interruption of the blood flow and a reduction of the mucosa prolapse.

This technique is actuated by use of a device with comprises a substantially cylindrical body with a stretcher function, exhibiting a grip and, in a lateral position, an opening or window for intercepting and observing a portion of prolapse.

The device further comprise a mobile wall which defines, in combination with the cylindrical body, a through-window which delimits an area of intervention and enables access from an internal cavity of the cylindrical body to the portion of prolapse.

More precisely, the mobile wall is slidably associated to the cylindrical body and can be displaced relatively thereto, such as to widen or narrow the area of intervention defined by the wall. In this way, it is possible to operate in a larger area without having to move the whole device.

In proximity of the window, the body comprises a seating for housing a probe (in particular an ultra-sound probe) which can detect the nearness of the blood vessel, in order to correctly direct the operating action of the suture even where there is poor accessibility or visibility in the area. The device further comprises means for illuminating, associable to the grip, for illuminating the zone interested by the operation and if necessary for diffusing the light in the cylindrical body.

Known-type devices are disadvantageously decidedly unwieldy for the operator to use.

During insertion of the device in the anal orifice, the mobile wall must not be displaced with respect to the cylindrical body and must be completely inserted therein, such that the window is in a configuration of minimum extension.

However, during the insertion, the distributed load exerted by the anal canal on the device tends to move the mobile wall and displace it from its operating position.

Consequently, during insertion of the device, the operator must take attention to maintain the mobile wall in its place. In other words, he or she must exert a counter-pressure on the mobile wall, together with the pressure on the rest of the device, in order to maintain the mobile wall in position.

For this reason, the use of devices of known type is particularly awkward for the operator.

When the inserted device has to be rotated, forces act on it to cause it to twist. During the rotation of the device, the load exerted by the anal canal generates a torque couple on the device, with a consequent displacing of the device itself. This deformation can determine a dissociation of the mobile wall from the cylindrical body. In this case, the device must be extracted and newly re-inserted, once the wall is reconnected to the body.

Consequently, in this case too, the operator must be particularly vigilant in order for the rotation of the device not to cause an involuntary separation of the mobile wall from the cylindrical body.

Thus, with reference to the foregoing, the technical objective of the present invention is to provide a device for surgical operations on a prolapse which does not present the mentioned drawbacks.

In particular, an aim of the present invention is to provide a device for surgical operations on a prolapse which is comfortable and easy to use.

Further, an aim of the present invention is to provide a device for surgical operations on a prolapse which enables rapid intervention which is as little traumatic as possible.

In the present invention, the technical objective and the aims as described are attained by a device for surgical intervention on a prolapse comprising the technical characteristics set out in one or more of the appended claims.

DISCLOSURE OF INVENTION

Further characteristics and advantages of the present invention will better emerge from the following description, provided by way of non-limiting example, of a preferred but non-exclusive embodiment of a device for surgical intervention on a prolapse, as illustrated in the accompanying figures of the drawings, in which:

FIG. 1 is a lateral plan view of the device for surgical operation on a prolapse according to the present invention;

FIG. 2 is a lateral plan view of the device of FIG. 1 in a different operative configuration;

FIGS. 3a and 3b illustrate perspective views of respective distinct parts of the device of FIG. 1.

Figure 4:
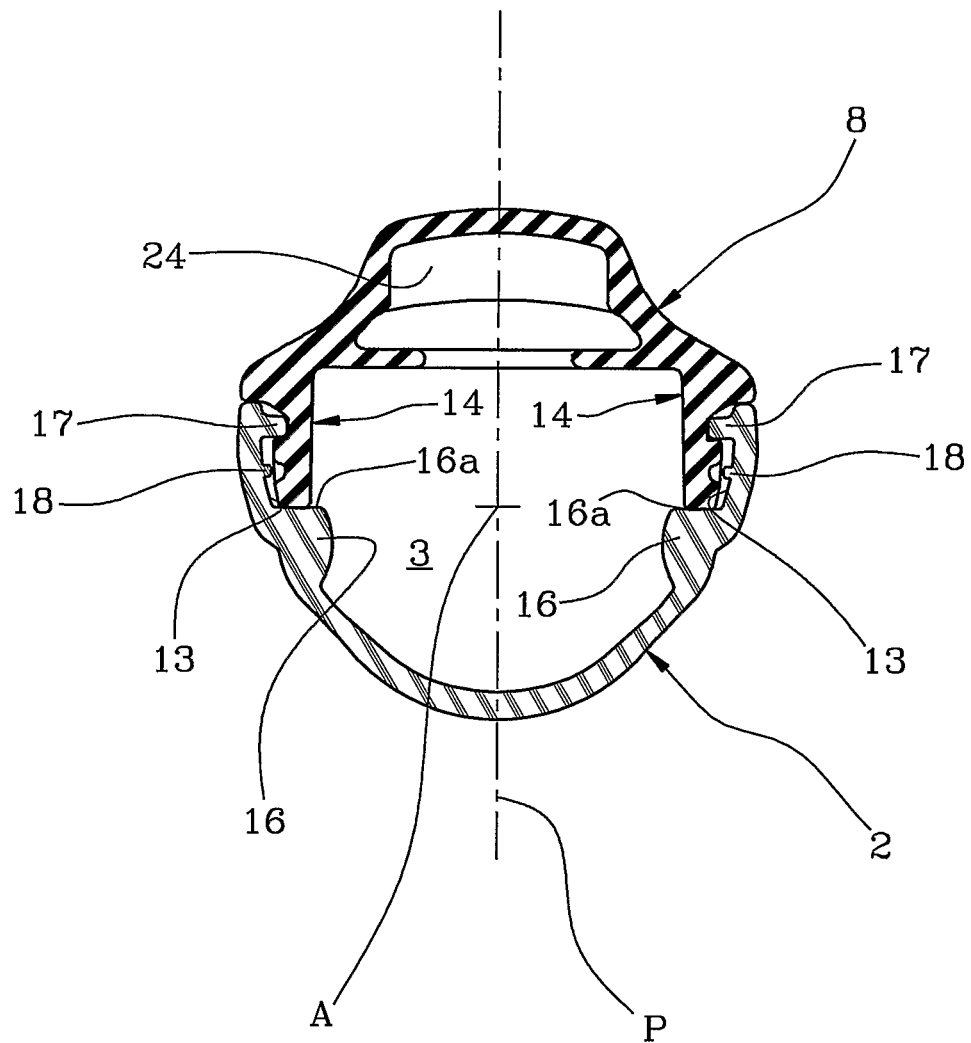
FIG. 4 is a transversal section view according to line IV-IV of FIG. 1.

With reference to the figures of the drawings, 1 denotes in its entirety a device for surgical operations on a prolapse.

The device 1 comprises a stretcher body 2 which is hollow and develops along a longitudinal axis A and exhibits a central portion 2a which is substantially cylindrical and defines, internally thereof, a cavity 3 which is the operating zone.

The central portion 2a is joined to an ogival closed front portion 2b that is also preferably tapered in order for the front portion 2b to be inserted in an anal orifice of a patient, reducing the trauma to a minimum for the patient.

The stretcher body 2 further comprises a truncoconical posterior portion 2c having a larger transversal size, in particular diverging towards the outside, for defining the maximum penetration of the stretcher body 2 internally of the anal orifice.

The posterior portion 2c is also hollow, to give accessibility to the cavity 3 to an external operator during the operation, accessibility being given to a posterior end 2c with reference to a penetration direction of the stretcher body 2 internally of the anal orifice.

The device 1 further comprises a grip 4 which is rigidly connected to the stretcher body 2. A housing channel 5 is afforded internally of the grip 4 (FIGS. 1 and 3b) in which means for illuminating are arranged (not illustrated in the figures of the drawings).

The means for illuminating are preferably made of an optic lighting fibre. The optic fibre is for example inserted at a free end 4a of the grip 4, and is then pushed until it reaches an operative position in which it emits a light which can reach the inside of the stretcher body 2, in order to illuminate the work zone (backlighting).

A first half-shell 6a is rigidly fixed to the posterior portion 2c of the stretcher body 2 and at least partially realises the grip 4 of the device 1. In the described embodiment, the housing channel 5 of the means for illuminating is wholly afforded in the first half-shell 6a.

The first half-shell 6a is coupled, preferably by male-female jointing means, to a second half-shell 6b, which completes the formation of the grip 4 of the device 1.

The stretcher body 2 exhibits a through-window 7 defining an operating area, and realising a communication between the cavity 3, and means for operating positioned internally of the cavity 3, and a rectal wall, with insertion of the device 1 complete. The window 7 thus enables easy access to a prolapse present on the rectal wall.

In the described embodiment, the window 7 is arranged in an opposite position to the grip 4 with respect to the stretcher body 2.

The window 7 advantageously has a variable extension, preferably in a parallel direction to the longitudinal axis A of the stretcher body 2. This is done by means of a mobile wall 8 associated to the stretcher body 2 and defining the through-window 7 in combination with the stretcher body 2.

The mobile wall 8 is slidably connected to the stretcher body 2 such as to open and/or to close the window 7 in order to change the extension thereof. In particular, the window 7 is configurable at least between a minimum-extension configuration and a maximum-extension configuration. The window 7 is further configurable in a plurality of intermediate configurations, corresponding to respective extensions comprised between the minimum and the maximum extensions.

The window 7 exhibits at least a first portion 7a, realised between the central portion 2a and the front portion 2b. The first portion 7a of the window 7 extends prevalently in a transversal direction to the longitudinal axis A in which the stretcher body 2 prevalently develops. Further, in the illustrated embodiment, the first portion 7a of the window is rectangular. The window 7 advantageously also exhibits a second portion 7b, preferably adjacent to the first portion 7a (FIG. 2). In the illustrated embodiment, the first portion 7a and the second portion 7b are communicating, and thus realise a single window 7. Further, the second portion 7b of the window 7 develops along the longitudinal axis A of the stretcher body 2, and extends preferably from the first portion 7a up to a posterior end 2d of the stretcher body 2. The second portion 7b can have any transversal dimensions, preferably greater than or equal to the transversal dimension of the first portion 7a.

The mobile wall 8 is slidably housed in the second portion 7b of the window 7 and can assume a plurality of operating positions between a closed position, in which it entirely obstructs the second portion 7b of the window 7, leaving only the first portion 7a accessible, and an open position, in which it entirely uncovers the second portion 7b of the window, which is thus entirely open and accessible from the outside.

In other words, when the mobile wall takes on the closed position, the window is in the minimum extension configuration, while when the mobile wall 8 is in the open position, the window 7 is in the maximum extension configuration, the mobile wall 8 being detached from the stretcher body 2. The movement of the mobile wall 8 between the closed position and the open position occurs in particular via a sliding thereof in a direction towards the posterior end 2d of the stretcher body 2.

The window's 7 increase in longitudinal extension, realised as above-described, is advantageous especially in a case of operations of ligature of the rectal artery in haemorrhoid pathology.

The mobile wall 8 of the device 1 of the present invention further comprises a gripping organ 9 which extends on an opposite side to the stretcher body 2 in order to grip and displace the mobile wall 8. The gripping organ 9 comprises a knurled flat portion 9a to further improve grip.

In a preferred embodiment, and illustrated in the enclosed figures, the mobile wall 8 is associated only to the second portion 7b of the window 7, while the first portion 7a is accessible from the outside even when the mobile wall 8 is in the closed position.

In the preferred and illustrated embodiment, the mobile wall 8 is substantially counter-shaped to the second portion 7b of the window 7 to which it is engaged, such that in the closed position there is no projection of the mobile wall 8 with respect to the normal surface of the stretcher body 2.

The device 1 further comprises blocking means 10 acting between the mobile wall 8 and the stretcher body 2 to maintain the wall 7 in the described configuration of minimum extension during the insertion of the stretcher body 2 into the patient's anal canal. In other words, the blocking means 10 act on the mobile wall 8 to maintain the wall 8 in the closed position during the insertion stage.

The blocking means 10 comprise at least an appendage 11 which is elastically associated to the mobile wall 8. The appendage 11 is insertable and extractable by snap-fit in a corresponding seating 12 afforded in the stretcher body 2 (FIG. 3b).

In more detail, the device 1 comprises two guides 13 which develop parallel to the longitudinal axis A and are afforded on the stretcher body 2. The device 1 also comprises two skates 14 which are rigidly connected to opposite sides of the mobile wall 8 and inserted slidably in the guides 13.

In the preferred embodiment, the blocking means 10 comprise two appendages 11, each elastically associated to a skate 14 and associable to two respective seatings 12 afforded in the stretcher body 2 (FIG. 3a).

In more detail, each skate 14 comprises a fixed portion 14a afforded in a single piece with the mobile body 8 and a projecting portion 14b which develops starting from the fixed portion 14a of the skate 14 towards a front end 2e of the stretcher body 2. Thus, the projecting portion 14b can oscillate elastically with respect to the fixed portion 14a.

Further, a tooth 14c is fashioned at only one of the two skates, which tooth 14c abuts against the corresponding sliding guide in order to compensate for any coupling tolerances between the skates 14 and guides 13.

The appendages 11 are advantageously arranged at the projecting portion 14b of each skate 14. In more detail, the appendages 11 are arranged at a front end 2a of the mobile wall 8.

Each seating 12 is aligned to the respective guide and is separated therefrom by a relief 15.

In use, the mobile wall 8 is associated to the stretcher body 2 such that each skate 14 is introduced in the respective seating 12. Thus, each skate 14 and the associated appendage 11 run along the guide 13 up until the appendage reaches the relief 15. With a further pressure, each appendage 11 passes beyond the relief 15, elastically flexing the projecting portion 14b of each skate 14 and thus reaching the corresponding seating 12.

When the device 1 is introduced into the patient's anal canal, the resulting force from the distributed load generated by the anal canal tends to push the mobile wall 8. However, the appendages 11 lie in contact against the respective reliefs 15 in order to prevent undesired displacements of the mobile wall 8 with respect to the stretcher body 2.

Should the operator exert a higher-intensity force on the mobile wall 8, the appendages 11 newly flex the projecting portion 14b and exit the respective seatings 12 in order to displace the mobile wall 8 with respect to the stretcher body. In this way, the window 7 can take on the desired configuration.

Each guide 13 comprises a respective wall 16 defining a respective flat surface 16a on which the respective skate 14 rests. Each wall 16 is perpendicular to a central plane of symmetry P, passing through the longitudinal axis A of the stretcher body 2 (FIG. 4). This characteristic advantageously gives greater stability to the device, and in particular the mobile wall 8.

Considering the elasticity of the tissue of the anal wall, it is known that on insertion of an extraneous body internally of the anal cavity the contractions of the patient push the body outwards from the cavity.

As for the whole device 1, with particular reference to the stretcher body 2, the body 2 remains inside the anal cavity thanks to the surgeon's intervention too.

As for the mobile wall 8, two different situations obtain.

In the condition in which the window 7 is in the minimum extension configuration, i.e. the mobile wall 8 is in the closed position, the blocking means 10 keep the mobile wall 8 in the stable position.

In the condition in which the window 7 is in a desired configuration, i.e. the mobile wall 8 is between the closed position and the open position, the friction which develops between each skate 14 and each respective flat rest surface 16a of the guide 13 newly guarantees the stability of the mobile wall 8 in the position reached.

The realisation of the flat rest surface 16a of the guide 13 enables the distributed load applied by the anal muscular tissue (which can be considered as a single force) to be split up into two corresponding constraint reactions, each of an intensity of half of the force applied to the muscular tissue.

The consequent friction force that develops between each rest surface 16a of the guide 13 and the skate 14, which is equal to the constraint reaction of the rest surface 16a for the typical friction coefficient of the chosen material, is maximum, as there are no other constraint reactions present than those counterposed to the resultant force applied by the muscular tissue.

Also, each guide 13 comprises a further wall 17 facing and parallel to the wall 16 that defines the rest surface 16a. Each skate 14 is completely inserted and runs between the wall 16 and the further wall 17 of the guide 13.

Each guide 13 also comprises a respective rib 18 which develops substantially from the posterior end 2d of the stretcher body 2 parallel to the wall 16 and the further wall 17 of each guide 13.

Each rib 18 extends from the stretcher body 2 towards the cavity 3 with a decreasing extension from the posterior end 2d towards the front end of the stretcher body 2.

Each rib 18 lies in contact with the respective skate 14 such that during the movement of the mobile wall 8 with respect to the stretcher body 2, the mobile wall 8 is subject to no dealignment and does not stick and block.

The device 1 further comprises anti-twist means 19 arranged between the stretcher body 2 and the mobile wall 8 in order to limit or prevent a torsional deformation of the device 1.

The anti-twist means 19 are arranged at the posterior end 2d of the stretcher body 2 and are active when the wall 7 is in the configuration of minimum extension.

The anti-twist means 19 comprise at least a projection 20 associated to the mobile wall 8 and insertable in a corresponding opening 21 afforded in the stretcher body 2.

In detail, the anti-twist means 19 comprise a pair of tabs connected to the stretcher body 2 at the posterior end 2d thereof. The tabs 22 are symmetrically arranged with respect to the central plane of symmetry P. The tabs 22 are coplanar to one another.

Further, the anti-twist means 19 comprise a corresponding pair of flanges 23 arranged symmetrically with respect to the central plane of symmetry P and coplanar to one another. The flanges 23 are fashioned at a posterior end of the mobile wall 8.

Two projections 20 are fashioned on the flanges 23 of the mobile wall 8 and are insertable in corresponding openings 21 afforded in the tabs 22 of the stretcher body 2. The openings 21 are countershaped with respect to the projections 20.

In particular, when the mobile wall 8 is in the closed position and the window is in the configuration of minimum extension, the tabs 22 face and are in contact with the flanges 23 and the projections 20 are inserted in the openings 21.

In this way, twisting actions determined by the torque load deriving from the rotation of the device inside the orifice are absorbed by the coupling between the projections 20 and the openings 21 between which the torque momentum unloads.

Thus, when the device 1 is inserted in the anal canal and is rotated, it neither twists nor bends. Consequently, the device 1 is sturdier and there is no involuntary separation between the stretcher body 2 and the mobile wall 8.

Sensors, not illustrated, can also be associated to the device 1, which sensors detect the pulsation of a vein or an artery, in particular the vicinity of the sensor to a rectal artery. The sensor means are preferably constituted by an ultrasound probe, and can advantageously be housed on the mobile wall 8, preferably removably, such as continuously to monitor the nearness of the rectal artery even during the sliding of the mobile wall 8.

For housing the sensors, the mobile wall 8 exhibits a dedicated housing 24, facing externally of the mobile wall 8, and, therefore, of the stretcher body 2, by means of an external terminal opening (FIG. 3a) realised on the mobile wall 8.

The external terminal opening 25, which sets the housing 24 in communication with the outside of the stretcher body 2, facilitates the detection of the rectal artery on the part of the sensors, by facing them up to the rectal wall and placing them in direct contact with the tissue, such that they can detect the proximity of the artery by detection of the associated blood flow.

The housing 24 is preferably also in communication with the cavity 3 of the stretcher body 2, in order to enable introduction of the sensors internally of the housing 24 through the posterior end 2d of the stretcher body 2.

The invention attains the set aims and provided important advantages.

The blocking means of the device for surgical operations on a prolapse of the present invention prevent the mobile wall from sliding during the stage of insertion of the device into the anal canal.

In this way, it is no longer necessary for the operator to perform specific manoeuvres aimed a keeping the mobile wall in place during this stage.

Also, any eventual stages of rotation of the device in the anal canal are simplified as the anti-twist means guarantee sufficient sturdiness of the device and prevent the mobile wall from exiting its seating.

The invention claimed is:

1. A device for surgical operations on a prolapse, comprising:
    a hollow stretcher body having a prevalent development direction along a longitudinal axis and being insertable in an orifice, the stretcher body having a closed front portion and exhibiting a lateral through-window, defining an area of intervention and adapted to realize a communication between an internal cavity of the stretcher body and a portion of a prolapse,
    a mobile wall defining the through-window in combination with the stretcher body and being slidably associated to the stretcher body in order to open and close the through-window between a configuration of minimum extension and a configuration of maximum extension of the through-window,
    wherein the mobile wall is movable according to a plurality of intermediate positions corresponding to intermediate configurations of the through window between the minimum and the maximum extensions of the through window;
    wherein the through window develops along the longitudinal axis of the stretcher body and the mobile wall is movable along the longitudinal axis of the stretcher body in such a way as to vary the extension of the through window in a direction parallel to the longitudinal axis of the stretcher body;
wherein the device comprises means for blocking which acts between the mobile wall and the stretcher body in order to maintain the through-window stably in the configuration of minimum extension during insertion of the stretcher body,
wherein the blocking means comprises at least one appendage which is elastically associated to the mobile wall and which is insertable and extractable by a snap-fit in a corresponding seating afforded in the stretcher body;
    wherein the device comprises two guides afforded in the stretcher body and two skates connected to respective opposite sides of the mobile wall and slidable in the guide; the at least one appendage comprising two appendages, each associated to a respective skate, and wherein the device further comprises two seatings, each of which is occupiable by a respective appendage; and
    wherein each skate comprises a fixed portion which is rigidly connected to the mobile wall and a projecting portion which projects from the fixed portion towards a front end of the stretcher body; each appendage being arranged on the projecting portion.

2. The device of claim 1, wherein each seating is aligned to a respective guide and is separated therefrom by a relief.

3. The device of claim 1, wherein each guide comprises at least one wall which is perpendicular to a central plane of symmetry and which defines a flat surface on which the skate rests.

4. The device of claim 3, wherein each guide further comprises a further wall facing and parallel to the wall; each skate being inserted between its respective wall and the further wall.

5. The device of claim 4, wherein each guide further comprises a respective rib developing from a posterior end of the stretcher body parallel to the wall and to the further wall, lying in contact with the skate in order to maintain the mobile wall aligned to the stretcher body.

6. The device of claim 1, wherein one of the two skates exhibits a tooth, destined to abut against a corresponding guide in order to compensate for any coupling tolerances between the skates and the guides.

7. The device of claim 1, wherein the device further comprises anti-twist means operatively arranged between the stretcher body and the mobile wall in order to limit a torque deformation of the device; the anti-twist means being arranged at a posterior end of the stretcher body and being active in the configuration of minimum extension of the through-window.

8. The device of claim 7, wherein the anti-twist means comprises at least one projection associated to the mobile wall and insertable in a corresponding opening afforded on the stretcher body.

9. The device of claim 8, wherein the at least one projection comprises two projections insertable in corresponding openings arranged symmetrically with respect to a plane of symmetry of the device.

10. The device of claim 9, wherein the stretcher body comprises two tabs arranged in proximity of the posterior end and symmetrically with respect to the plane of symmetry on which the openings are respectively afforded.

11. The device of claim 9, wherein the mobile wall comprises two flanges arranged symmetrically with respect to the central plane of symmetry on which the projections are arranged.

12. The device of claim 1, wherein the mobile wall comprises a gripping organ extending on an opposite side with respect to the stretcher body for gripping and displacing the mobile wall with respect to the stretcher body.

13. The device of claim 1, wherein the device further comprises a grip, fixed to the stretcher body, the grip defining internally thereof a seating for housing a means for illuminating.

14. The device of claim 1, wherein the mobile wall comprises a housing for removably containing sensors for detecting a vicinity of a haemorrhoidal artery.

15. A device for surgical operations on a prolapse, comprising:
- a hollow stretcher body having a prevalent development direction along a longitudinal axis and being insertable in an orifice, the stretcher body having a closed front portion and exhibiting a lateral through-window, defining an area of intervention and adapted to realize a communication between an internal cavity of the stretcher body and a portion of a prolapse,
- a mobile wall defining the through-window in combination with the stretcher body and being slidably associated to the stretcher body in order to open and close the through-window between a configuration of minimum extension and a configuration of maximum extension of the through-window,
- wherein the mobile wall is movable according to a plurality of intermediate positions corresponding to intermediate configurations of the through window between the minimum and the maximum extensions of the through window;
- wherein the through window develops along the longitudinal axis of the stretcher body and the mobile wall is movable along the longitudinal axis of the stretcher body in such a way as to vary the extension of the through window in a direction parallel to the longitudinal axis of the stretcher body;
- wherein the device comprises means for blocking which acts between the mobile wall and the stretcher body in order to maintain the through-window stably in the configuration of minimum extension during insertion of the stretcher body;
- wherein the blocking means comprise at least one appendage which is elastically associated to the mobile wall and which is insertable and extractable by a snap-fit in a corresponding seating afforded in the stretcher body;
- wherein the device comprises two guides afforded in the stretcher body and two skates connected to respective opposite sides of the mobile wall and slidable in the guide; the at least one appendage comprising two appendages, each associated to a respective skate, and wherein the device further comprises two seatings, each of which is occupiable by a respective appendage; and
- wherein one of the two skates exhibits a tooth, destined to abut against a corresponding guide in order to compensate for any coupling tolerances between the skates and the guides.

16. A device for surgical operations on a prolapse, comprising:
- a hollow stretcher body having a prevalent development direction along a longitudinal axis and being insertable in an orifice, the stretcher body having a closed front portion and exhibiting a lateral through-window, defining an area of intervention and adapted to realize a communication between an internal cavity of the stretcher body and a portion of a prolapse,
- a mobile wall defining the through-window in combination with the stretcher body and being slidably associated to the stretcher body in order to open and close the through-window between a configuration of minimum extension and a configuration of maximum extension of the through-window,
- wherein the mobile wall is movable according to a plurality of intermediate positions corresponding to intermediate configurations of the through window between the minimum and the maximum extensions of the through window;
- wherein the through window develops along the longitudinal axis of the stretcher body and the mobile wall is movable along the longitudinal axis of the stretcher body in such a way as to vary the extension of the through window in a direction parallel to the longitudinal axis of the stretcher body;
- wherein the device comprises means for blocking which acts between the mobile wall and the stretcher body in order to maintain the through-window stably in the configuration of minimum extension during insertion of the stretcher body,
- wherein the blocking means comprises at least one appendage which is elastically associated to the mobile wall and which is insertable and extractable by a snap-fit in a corresponding seating afforded in the stretcher body;
- wherein the device further comprises anti-twist means operatively arranged between the stretcher body and the mobile wall in order to limit a torque deformation of the device; the anti-twist means being arranged at a posterior end of the stretcher body and being active in the configuration of minimum extension of the through-window;
- wherein the anti-twist means comprises two projections associated to the mobile wall and insertable in corresponding openings afforded on the stretcher body and arranged symmetrically with respect to a plane of symmetry of the device; and
- wherein the stretcher body comprises two tabs arranged in proximity of the posterior end and symmetrically with respect to the plane of symmetry on which the openings are respectively afforded.

17. A device for surgical operations on a prolapse, comprising:
- a hollow stretcher body having a prevalent development direction along a longitudinal axis and being insertable in an orifice, the stretcher body having a closed front portion and exhibiting a lateral through-window, defining an area of intervention and adapted to realize a communication between an internal cavity of the stretcher body and a portion of a prolapse,
- a mobile wall defining the through-window in combination with the stretcher body and being slidably associated to the stretcher body in order to open and close the through-window between a configuration of minimum extension and a configuration of maximum extension of the through-window, wherein the mobile wall is movable according to a plurality of intermediate positions corresponding to intermediate configurations of the through window between the minimum and the maximum extensions of the through window;

wherein the through window develops along the longitudinal axis of the stretcher body and the mobile wall is movable along the longitudinal axis of the stretcher body in such a way as to vary the extension of the through window in a direction parallel to the longitudinal axis of the stretcher body;

wherein the device comprises means for blocking which acts between the mobile wall and the stretcher body in order to maintain the through-window stably in the configuration of minimum extension during insertion of the stretcher body;

wherein the blocking means comprises at least one appendage which is elastically associated to the mobile wall and which is insertable and extractable by a snap-fit in a corresponding seating afforded in the stretcher body;

wherein the device further comprises anti-twist means operatively arranged between the stretcher body and the mobile wall in order to limit a torque deformation of the device; the anti-twist means being arranged at a posterior end of the stretcher body and being active in the configuration of minimum extension of the through-window;

wherein the anti-twist means comprises two projections associated to the mobile wall and insertable in corresponding openings afforded on the stretcher body and arranged symmetrically with respect to a plane of symmetry of the device; and wherein the mobile wall comprises two flanges arranged symmetrically with respect to the central plane of symmetry on which the projections are arranged.

* * * * *